United States Patent [19]

Montoya

[11] Patent Number: 5,486,099
[45] Date of Patent: Jan. 23, 1996

[54] PERISTALTIC PUMP WITH OCCLUSIVE INLET

[75] Inventor: Jean P. Montoya, Ann Arbor, Mich.

[73] Assignee: Michigan Critical Care Consultants, Inc., Ann Arbor, Mich.

[21] Appl. No.: 355,700

[22] Filed: Dec. 14, 1994

[51] Int. Cl.⁶ .............................. F04B 43/08; F16L 11/08
[52] U.S. Cl. ...................... 417/477.13; 138/119; 138/128
[58] Field of Search .......................... 417/477.13, 477.1, 417/474, 476, 479, 480; 138/157, 119, 128; 251/4, 6, 7

[56] References Cited

U.S. PATENT DOCUMENTS

| | | | |
|---|---|---|---|
| 562,902 | 6/1896 | Messmer | 417/476 |
| 2,123,781 | 7/1938 | Huber | 417/476 |
| 3,295,556 | 1/1967 | Gertsma et al. | 138/119 |
| 3,403,631 | 10/1968 | Tangeman | 417/477.13 |
| 4,066,238 | 1/1978 | Clarke | 251/6 |
| 4,087,301 | 5/1978 | Steadman | 251/6 |
| 4,131,399 | 12/1978 | Calvet | 417/477 |
| 4,275,761 | 6/1981 | Waldhauser | 137/595 |
| 4,478,661 | 10/1984 | Lewis | 156/92 |
| 4,515,589 | 5/1985 | Austin et al. | 604/122 |
| 4,540,350 | 9/1985 | Streicher | 417/478 |
| 4,650,471 | 3/1987 | Tamari | 604/153 |
| 4,767,289 | 8/1988 | Parrott et al. | 417/477 |
| 4,954,055 | 9/1990 | Raible | 138/119 |
| 5,067,879 | 11/1991 | Carpenter | 138/119 |
| 5,088,522 | 2/1992 | Rath et al. | 138/119 |
| 5,215,450 | 6/1993 | Tamari | 417/474 |
| 5,222,880 | 6/1993 | Montoya et al. | 417/477.13 |
| 5,281,112 | 1/1994 | Montoya et al. | 417/477 |
| 5,342,182 | 8/1994 | Montoya et al. | 417/477.1 |

*Primary Examiner*—Richard A. Bertsch
*Assistant Examiner*—Peter G. Korytnyk
*Attorney, Agent, or Firm*—Harness, Dickey & Pierce

[57] ABSTRACT

A peristaltic pump having a pump conduit with an occlusive inlet segment. The pump includes a frame with rollers carried by rotor and rotated by a motor. A flexible conduit having an inlet end and an outlet end is positioned around the rollers and includes an occlusive segment and non-occlusive segment. In its free condition, the occlusive segment is collapsed and the passageway through it substantially completely occluded when the pressure within the occlusive segment is equal to or less than pressure acting on the outside of the occlusive segment. The non-occlusive segment is mildly biased to exhibit an inflated condition with an open passage when in its free condition with the pressure within the non-occlusive segment equal to pressure acting on the outside of the non-occlusive segment.

17 Claims, 6 Drawing Sheets

PERISTALTIC PUMP WITH OCCLUSIVE INLET

STATEMENT OF GOVERNMENTAL SUPPORT

This invention was made with support from the U.S. Government under Grant No. 5 R44 HL46613-03 awarded by the National Institutes of Health. The U.S. Government has certain rights in this invention.

BACKGROUND OF THE INVENTION

1. Field of the Invention

The present invention generally relates to peristaltic pumps. More particularly, this invention relates to a peristaltic pump in which the pumping conduit is integrally formed with two portions. The first portion is an occlusive portion that completely occludes when the pressure within this portion is equal to or less than pressure acting on it. The second portion is a non-occlusive portion which is slightly biased so that this portion will be inflated, defining an open passageway, when pressure within it is not substantially less than pressure acting on its outside.

2. Description of the Prior Art

Peristaltic pumps have been used with significant success in a wide range of extracorporeal circulation procedures. Generally, during extracorporeal circulation, blood or other bodily fluids are transferred between a patient and one or more extracorporeal devices which process the fluid before it is returned to the patient. Medical procedures which commonly employ such pumps include, without limitation, the following: open heart surgery, dialysis procedures and long term continuous care situations. During open heart surgery, blood is transferred by the pump between a patient and multiple blood processing devices such as a defoamer, oxygenator and a heater. During dialysis procedures, the pump passes the blood through a dialyzer which removes impurities. In a long term continuous care situation, intravenous solutions are slowly infused by the pump through a venous catheter into the patient, for either general distribution or localized treatment.

Peristaltic pumps can be described as volumetric pumps which include a movable or rotating member having rollers that will compress a flexible pump conduit at spaced apart intervals. The successive of compression of the conduit and the relative movement of this compression point along the length of the conduit, forces the fluid through the conduit. Its simplicity of operation and the absence of direct contact between the pumped fluid and the various pump components are two of the principal advantages of a peristaltic pump.

While used with considerable success, some peristaltic pump designs exhibit certain inherent limitations. Obviously, these limitations must be taken into consideration during the use of the pump. For example, some peristaltic pumps use non-occlusive conduits that are progressively compressed by the rollers against a raceway or stator and are driven by constant speed motors. A non-occlusive conduit has a normally open passageway defined through its center. These pumps draw blood at a substantially constant rate. If the fluid circuit becomes occluded downstream of such a pump, the pump can overpressurize the conduit resulting in rupture. Additionally, if the upstream supply of fluid to the pump stops because of an occlusion, the pump will generate negative pressures downstream of the occlusion. When low enough, the pressure will damage or hemolyze the blood and/or result in the emptying of the fluid supply vessel. If the fluid supply is emptied, the possibility exists for the supply tissue vessel of the patient to collapse, resulting in damage to the tissue at the drainage catheter tip.

Another type of peristaltic pump includes a non-occlusive double walled conduit in which the inner conduit is constructed of thin wall resilient material that can collapse when the pressure acting inside is equal or below the pressure acting outside the conduit. This type of peristaltic pump is described in U.S. Pat. No. 4,515,589. While this pump cannot generate significant negative pressures at their inlets upon upstream occlusion, if the outlet is occluded, overpressurization can result because the conduit is forcefully compressed by the rollers against a raceway or stator.

Another type of peristaltic pump includes an occlusive conduit. These types of pumps are constructed so that when pressure inside of the conduit is equal to or lower than the pressure acting on the outside of the conduit, the conduit will be substantially occluded over its length. One such pump is disclosed in U.S. Pat. No. 5,222,880. While a pump of this variety is incapable of generating negative pressures when the supply of fluid to the pump is stopped, in order to operate and overcome the inherent tension of the tubing, the pump requires inlet fluid pressures and flow rates which, at times, may be greater than that which is desired or available.

In view of the above disadvantages and limitations, it can be seen that there is still a need in the art to provide an improved peristaltic pump which avoids producing negative pressures upstream of the pump inlet, which cannot overpressurize downstream from the pump outlet, and which is capable of filling and pumping a greater amount of blood at a lower inlet pressures compared to pumps that are normally occluded along their length.

It is therefore a principle object of the present invention to provide a peristaltic pump which requires lower inlet pressures in order to fill and pump a significant quantity of blood.

It is another object of the present invention to provide a peristaltic pump which will cease to pump blood when the blood supply filling pressure is equal to or falls below the pressure acting on the outside of the pump inlet.

A further object of the present invention is to provide a peristaltic pump which is unable to generate subatmospheric pressures upstream from the pump inlet.

Still another object of this invention is to provide a peristaltic pump which will cease to pump a fluid when the fluid supply filling pressure is equal to or falls below the pressure acting on the outside of the pump's inlet.

It is also an object of this invention to provide a peristaltic pump which can generate a slight subatmospheric pressure downstream from its inlet when the fluid supply filling pressure is equal to or less than the pressure acting on the outside of the pump chamber.

It is yet another object of this invention to provide a peristaltic pump which is incapable of overpressurizing when the outlet is occluded.

The present invention achieves the above and other objects by providing a peristaltic pump, without a raceway or stator, that uses a pump conduit wrapped under tension around rollers mounted on a rotatable rotor. The pump conduit is made of a resilient material and normally exhibits a slightly biased condition along its length except for a small segment of its length located adjacent to the inlet of the pump. This inlet segment of the pump conduit is formed so that it is completely occluded when the pressure inside the pump conduit is equal to or less than the pressure acting on the outside of the pump conduit. The inlet segment or occlusive portion of the pump conduit begins upstream from the location where the rotating rollers first engage the pump conduit and may or may not extend slightly into the region engaged by the rotating rollers.

When constructed in the above manner, the peristaltic pump will pump blood or another fluid as long as the fluid supply filling pressure is above the pressure acting on the outside of the pump chamber. The fluid will cease to be pumped when the fluid supply or filling pressure is equal to or falls below the pressure acting on the outside of the pump chamber. This occurs even if the rotor of the pump continues to operate and rotate. As a result, negative relative pressures cannot be generated upstream from the occluded inlet segment of the pump conduit. When the occlusive segment is completely occluded, however, the pump can generate, slight subatmospheric pressures downstream from the occlusive segment if the rotor continues to rotate. These slight subatmospheric pressure, however, are insufficient to cause damage to the blood cells.

Another advantage of this pump conduit design is that the pump is capable of filling and pumping more fluid at lower filling pressures in comparison to pumps having pump conduits which are occlusive along their entire length.

Another advantage is that when used with a reservoir located upstream from the peristaltic pump, the present invention would prevent the reservoir emptying and potentially pumping air into a patient.

Additional benefits and advantages of the present invention will become apparent to those skilled in the art to which the present invention relates from the subsequent description of the preferred embodiment and the appended claims, taken in conjunction with the accompanying drawings.

DETAILED DESCRIPTION OF THE PREFERRED EMBODIMENT

Figure 1:
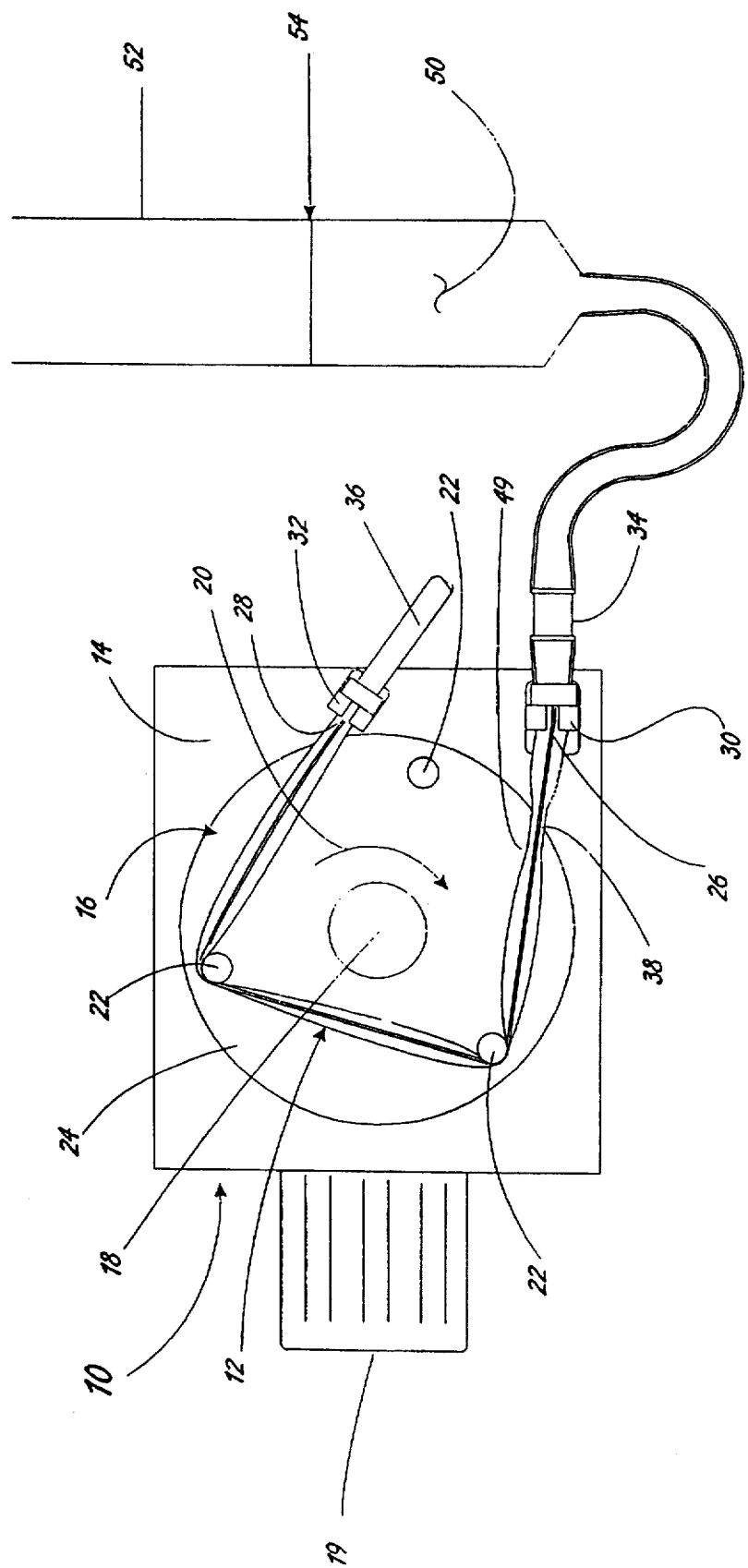
FIG. 1 is a diagrammatic illustration of a peristaltic pump embodying the principles of the present invention when the fluid filling pressure is greater than the pressure acting on the outside of the occlusive inlet segment of the pump conduit.

Referring now to the drawings in greater detail, a peristaltic pump 10 embodying the principles of the present invention is illustrated in FIG. 1 and generally designated at 10. It is anticipated that the pump 10 of the present invention will have a broad range of utility in a wide variety of pumping application, in particular extracorporeal applications including, but not limited to, cardiopulmonary bypass, blood oxygenation, carbon dioxide removal, hemodialysis and blood filtration as well as long term continuous care situations such as those requiring medicant infusion.

Principally, the pump 10 is comprised of a pump conduit or tube 12, a frame 14 and a wheel or rotor 16. The rotor 16 is mounted to the frame 14 for rotation about an axis defined by a shaft 18 centrally positioned in the rotor 16. Driving the shaft 18 is an electric motor 19 or other suitable driving means which causes the rotor 16 to rotate in a clockwise direction which is indicated by arrow 20.

Extending from the rotor 16, generally parallel with the shaft 18, are a plurality of rollers 22. The rollers 22 are radially positioned around the rotor 16 at equal distances and, as the rotor 16 is rotated, the rollers 22 move in a generally circular path. In the illustrated embodiment, three rollers 22 are shown as being spaced approximately 120° apart. The rollers 22 themselves are mounted for rotation about their own axes. Thus, as the rollers 22 move along the pump conduit 12, the rollers 22 will not produce a significant amount of frictional pull or tension on the conduit 12 thereby increasing its useful life.

As the skilled artisan will appreciate, the actual number of rollers utilized will depend on the specific application and could be varied without departing from the nature of the present invention. Alternatively, the rotor 16 could be designed to carry the rollers 22 in a non-circular path. For the sake of clarity, the rollers 22 are also illustrated as extending from a single plate 24. However, the rollers 22 can extend between a pair of plates (an interior plate and an exterior plate) which would cooperate to prevent the conduit 12 from inadvertently coming off of the rollers 22.

The conduit 12 is constructed of a flexible material, such as surgical grade polyurethane or other suitable material, and is positioned so as to extend around the rollers 22 with its inlet end 26 and outlet end 28 respectively secured to an inlet coupling 30 and an outlet coupling 32. The couplings 30 and 32 are in turn mounted to the frame 14 of the pump 10 and connect the conduit 12 to an inlet supply conduit 34, which delivers the desired fluid to the pump 10, and an outlet supply conduit 36, which directs the fluid back to the patient or to another extracorporeal device.

While not shown, a housing may be mounted to the frame 14 to protectively enclose the conduit 12 and rotor 16. If desired, the housing can be hinged with respect to the frame 14 to readily permit access to the various components of the pump 10.

Referring now to FIGS. 4a, 4b, 5, 6 and 7, it is seen that the conduit 12 is generally unitarily formed with two integral portions herein referred to as an occlusive or first segment 38 and a non-occlusive or second segment 40. The occlusive segment 38 occupies a lesser of the conduit's length than the non-occlusive portion 40 for reasons more fully discussed below.

The principal difference between the two segments is that the occlusive segment 38 is naturally flat and the passageway 42 therethrough is fully occluded when no blood is being supplied to the pump 10 through the inlet supply conduit 34. Stated another way, when the external pressure acting on the outside of the occlusive segment 38 is at least equal to the pressure on the inside of the occlusive segment 38, the occlusive portion will collapse into a fully occluded state. This is herein referred to as the "free" condition of the occlusive segment 38. When fully occluded, the occlusive segment 38 makes it impossible for negative pressures to be generated within the occlusive segment 38 or upstream of the segment 38. If the rotor 16 continues to rotate after occlusion of the occlusive segment 38, the present invention prevents emptying of the upstream conduit 34, collapsing of the supply tissue (with its potential for damage) and the pumping of air into the patient.

To ensure that the occlusive portion 38 is fully occluded when in its free condition or that negative pressures can not be generated within the occlusive segment 38, the conduit 12 in the area of the occlusive segment 38 exhibits an inner radius of curvature 44 which is or approaches zero at its side edges 46. Methods of constructing such a conduit 12 are known in the industry. In one method of construction, a thin walled tubing of flexible material, such as polyurethane or vinyl, is heat treated and permanently deformed into this free condition shape. Another method of constructing the occlusive segment 38 involves adhering two films or sheets of flat, flexible material together along their longitudinal edges 46. The edges 46 may be adhered by heat sealing or by the use of adhesives.

When mounted over the rollers 22, the occlusive segment 38 of the conduit 12 is oriented so that the side edges of the occlusive segment 38 are longitudinally spaced along the rotational axes of the rollers 22 such that a flat side 48 of the occlusive segment 38 is in surface-to-surface contact with the circumferential surfaces of the rollers 22.

Figure 5:
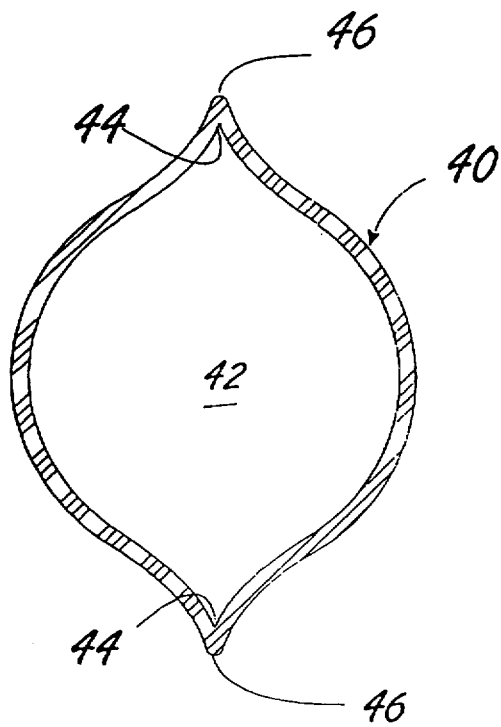
FIG. 5 is a cross-sectional view taken substantially along line 5—5 in FIG. 4b of the non-occlusive segment of the pump conduit.
Figure 6:
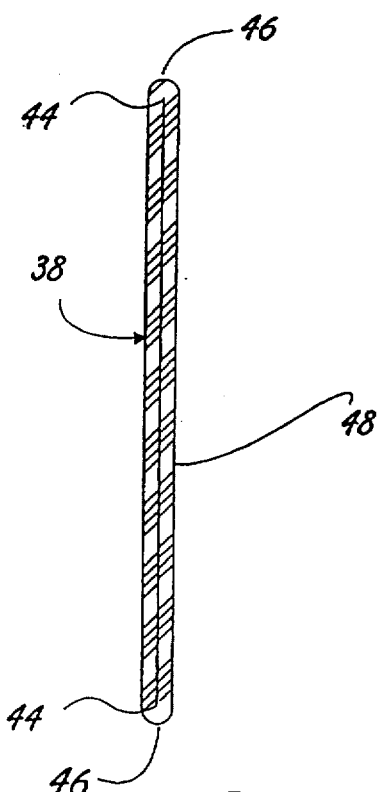
FIG. 6 is a cross-sectional view taken substantially along the line 6—6 in FIG. 4b illustrating the occlusive inlet segment of the pump conduit in an occluded condition.

The non-occlusive segment 40 exhibits a mild bias so that the passageway 42 through it is open when the non-occlusive segment 40 is in its free condition. However, to ensure that the non-occlusive portion 40 is fully occluded when in its collapsed condition, and that finite negative pressures can only be generated within the non-occlusive segment 40, the conduit 12 in the area of the non-occlusive segment 40 preferably exhibits an inner radius of curvature 44 which is or approaches zero at its side edges 46, similar to the occlusive segment 38. Accordingly, when the pressure within the passageway 42 in the non-occlusive segment 40 is equal to the pressure acting on the outside of the non-occlusive segment 40, the passageway 42 will be open as seen in FIG. 5. This allows slight, but finite, negative pressures to be generated in the conduit 12 even as the rotor 16 continues to rotate. Also, by not being occlusive along its entire length, the conduit 12 requires decreased inlet pressures and flow rates thereby allowing a greater amount of fluid to be initially pumped with less effort and priming.

With the conduit 12 located about the rollers 22 of the pump 10, it can be seen (in FIG. 1) that the occlusive segment 38 begins upstream from the position where the rollers 22 first engage the conduit 12 during rotation and may, but need not, extend slightly into the region engaged by the rollers 22 and the conduit 12. The area of first engagement between the rollers 22 and the conduit 12 is generally illustrated in FIG. 1 at 49.

Figure 7:
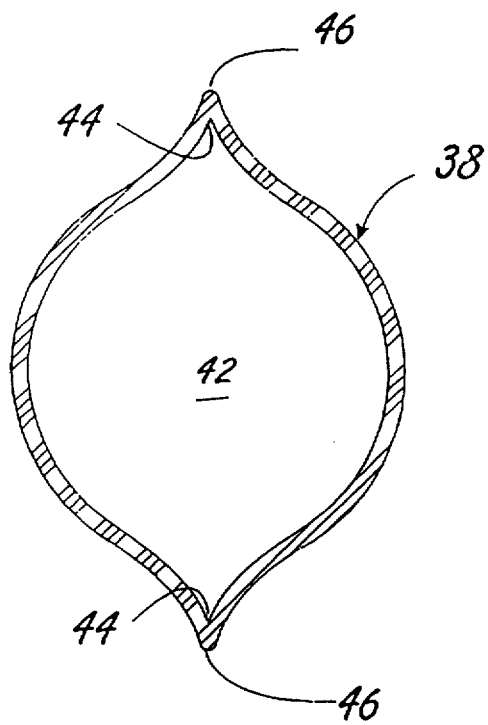
FIG. 7 is a cross-sectional view through the occlusive inlet segment of FIG. 6 in a non-occluded state.

When the fluid inlet supply pressure is greater than the pressure acting on the exterior of the conduit 12, the occlusive segment 38 will inflate and fill with fluid 50 and the pump 10 will force the fluid 50 through the outlet supply conduit 36 as a result. In its inflated state, the occlusive segment 38 assumes a general lemon shape as seen in FIG. 7. One situation where the inlet fluid pressure is greater than the exterior pressure on the conduit 12 is when the fluid 50 is contained within and received into a reservoir 52 whose level 54 of the fluid 50 is above the level defining the inlet end 26 of the conduit 12 and pump 10. This is seen in FIG. 1. Because the occlusive segment 38 only occupies a relatively small length of the conduit 12, the present invention is capable of filling and pumping more fluid at lower filling pressures than pumps having conduits which are occlusive along their entire lengths.

Figure 2:
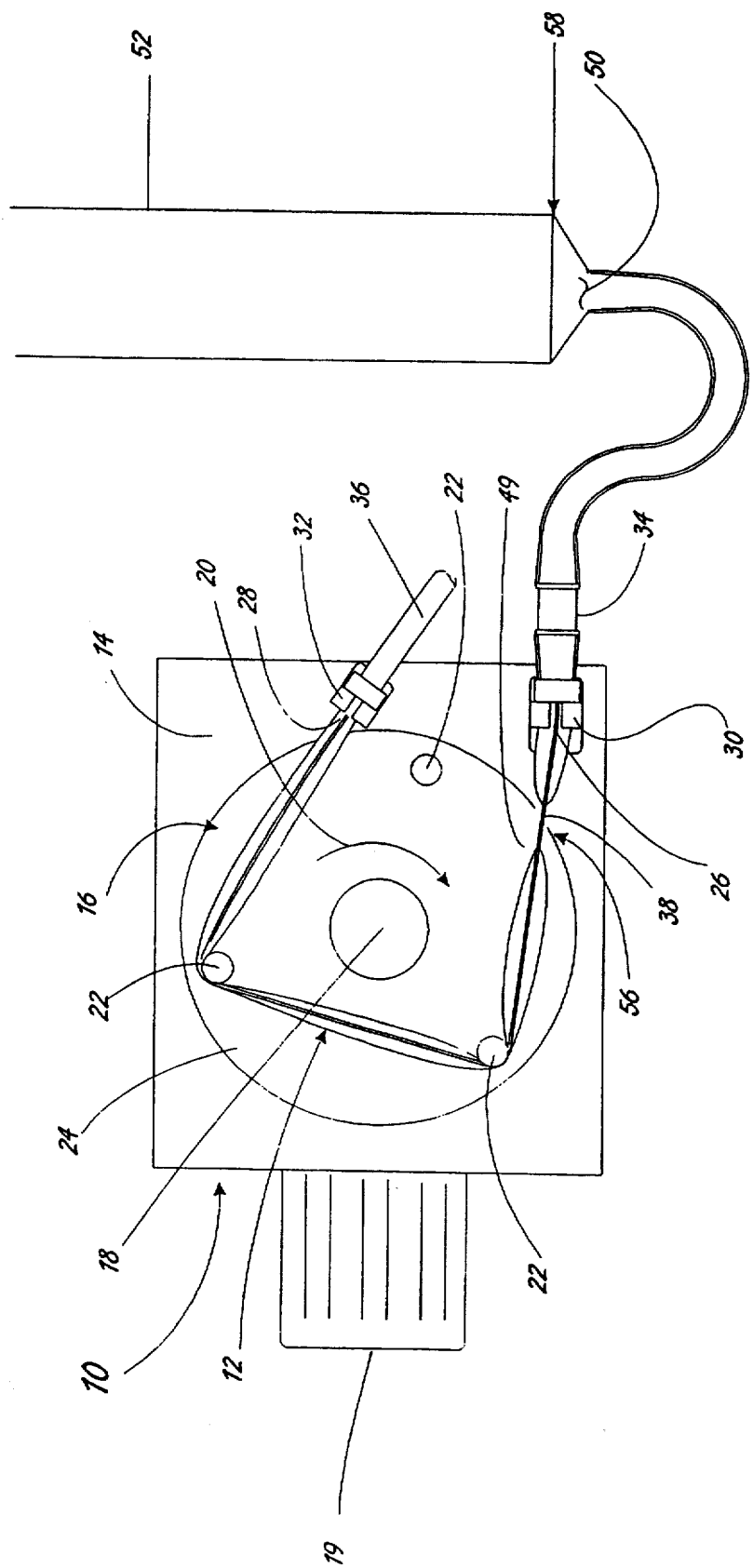
FIG. 2 is a diagrammatic illustration of a peristaltic pump embodying the principles of the present invention and illustrating the occlusive inlet segment of the pump conduit when the supply fluid pressure is equal to the pressure acting on the outside of the pump conduit.

When the fluid pressure at the inlet end 26 of the conduit is equal to the pressure acting on the outside of the occlusive segment 38, the occlusive segment 38 will assume its free condition thereby completely closing the passageway 42 of the occlusive segment 38 designated at 56 in FIG. 2. One situation where this would occur is when the level 58 of the fluid 50 in the reservoir 52 first corresponds with the height of the inlet end 26 of the pump 10.

Figure 3:
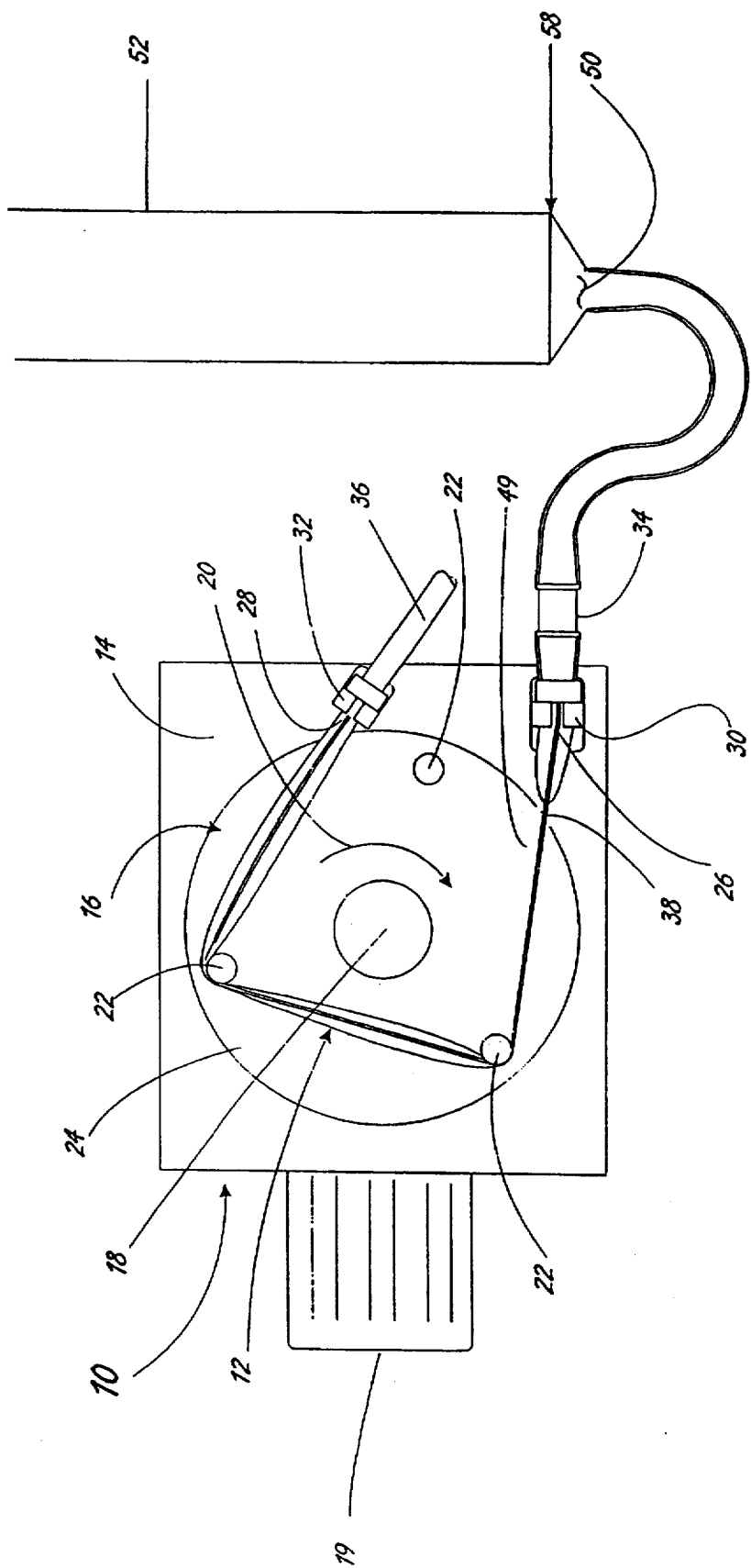
FIG. 3 is a diagrammatic illustration of a peristaltic pump embodying the principles of the present invention when the fluid filling pressure is equal or below the pressure on the outside of the pump conduit and after the development of slight negative pressures in the non-occlusive segment of the pump conduit.
Figure 4A:
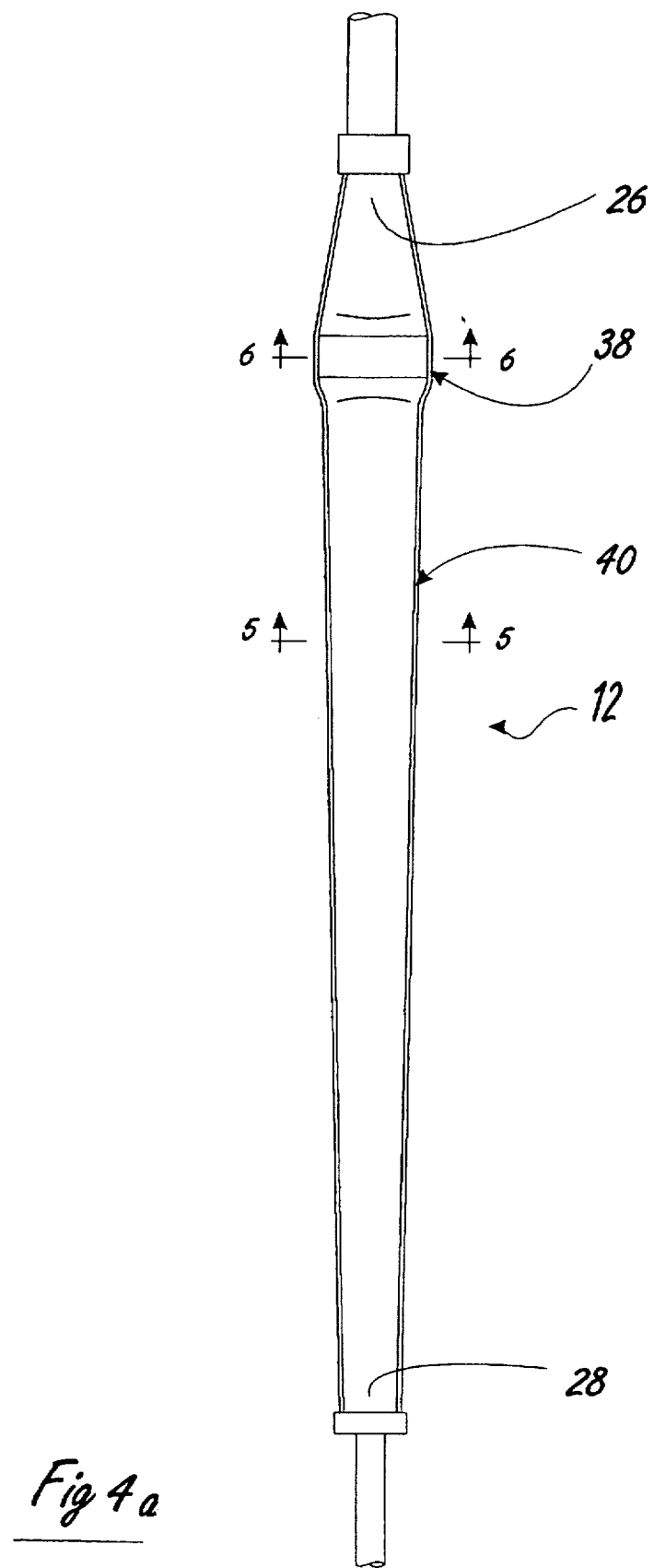
FIGS. 4a and 4b are plan and lateral views of one embodiment of a pump conduit as utilized in a peristaltic pump embodying the principles of the present invention.
Figure 4:
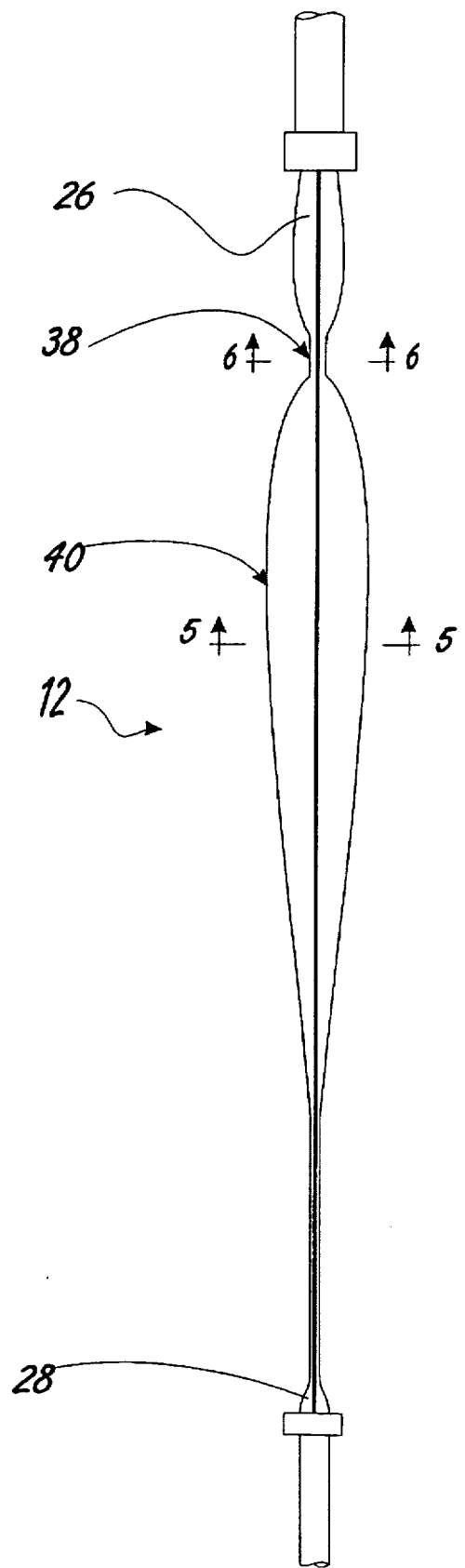

As seen in FIG. 3, as the rotor 16 continues to rotate and move the rollers 22 along the length of the conduit 12, all of the fluid filling the passageway 42 of the non-occlusive segment 40 will be progressively forced out of the pump 10 without any additional fluid 50 being drawn into it through the occlusive segment 38. Resultingly, the non-occlusive segment 40 initially experiences a collapse as relative pressures are generated within the non-occlusive segment 40 of the conduit 12. Because of the occlusive segment 38, the present invention is incapable of generating negative pressures at the inlet end 26 or upstream therefrom. A pump which incorporates a non-occlusive or normally inflated conduit about its entire length would be capable of generating these upstream negative pressures and potentially collapsing the supply conduit and damaging tissue of the patient as a result of the catheter tip being located in the supply tissue vessel.

While the above description constitutes the preferred embodiment of the present invention, it will be appreciated that the invention is susceptible to modification, variation and change without departing from the proper scope and fair meaning of the accompanying claims.

I claim:

1. A peristaltic pump for pumping fluids comprising:

a frame having a plurality of rollers and carrier means for carrying said rollers in spaced apart relation along a predetermined path;

drive means for causing movement of said carrier means thereby inducing said rollers to move along said predetermined path;

a flexible conduit having integrally formed first and second segments located between an inlet end and an outlet end, said first segment located upstream from said second segment and said first segment being collapsed and a passageway therethrough being substantially completely occluded in a free condition when pressure within said first segment is equal to pressure acting on the outside of said first segment thereby preventing the transmission of fluids therethrough, said first segment assuming an inflated condition having an unobstructed passageway when pressure within said first segment is greater than the pressure acting on the outside of said first segment thereby permitting the transmission of fluids therethrough, said second segment being biased to exhibit an inflated condition with an open passage therethrough in a free condition when pressure within said second segment is equal to pressure acting on the outside of said first segment thereby permitting the transmission of fluid therethrough; and mounting means for engaging said inlet and outlet ends and for mounting said conduit about said rollers whereby said conduit cooperates along part of its length with said rollers without use of a stator to thereby transmit fluid through said conduit by peristaltic movement.

2. A peristaltic pump according to claim 1 wherein said first segment exhibits an inflated state having an unoccluded passageway therethrough when pressure within and upstream of said first segment is greater than the pressure acting on the outside of said first segment.

3. A peristaltic pump according to claim 1 wherein said first segment is shorter in length than said second segment.

4. A peristaltic pump according to claim 1 wherein said first segment is located such that said first segment is not engaged by said rollers as said rollers are rotated, said second segment cooperating along at least part of its length so as to be engaged with said rollers whereby said rollers at least partially collapse said second segment so as to transmit fluids through said conduit by peristaltic movement.

5. A peristaltic pump according to claim 1 wherein said first and second segments are unitarily formed with each other.

6. A peristaltic pump according to claim 1 wherein only said second segment is engagable with said rollers.

7. A peristaltic pump according to claim 6 wherein said second segment is located such that said rollers engage said second segment substantially adjacent to said first segment.

8. A peristaltic pump according to claim 1 wherein said rotor rotates and said predetermined path is circular.

9. A peristaltic pump according to claim 1 wherein said peristaltic pump does not utilize a stator to collapse said second segment.

10. A peristaltic pump according to claim 1 wherein said conduit is located about rollers such that said first segment is engagable with said rollers.

11. A peristaltic pump for pumping fluids comprising a frame having a plurality of rollers and carrier means for carrying said rollers in spaced apart relation along a predetermined path, drive means for causing movement of said carrier means thereby inducing said rollers to move along said predetermined path, a flexible conduit having unitarilly formed first and second segments located between an inlet end and an outlet end, said first segment located upstream from said second segment, said first segment being collapsed and said passageway therethrough being substantially completely occluded in a free condition when pressure within said first segment is equal to pressure acting on the outside of said first segment thereby preventing the transmission of fluids therethrough, said first segment assuming an inflated condition having an unobstructed passageway when pressure within and upstream of said first segment is greater than the pressure acting on the outside of said first segment thereby permitting the transmission of fluids therethrough, said second segment being longer in length than said first segment and being biased to exhibit an inflated condition with an open passage therethrough in a free condition when pressure within said second segment is equal to pressure acting on the outside of said first segment thereby permitting the transmission of fluid therethrough, said second segment cooperating along at least part of its length so as to be engaged with said rollers whereby said rollers at least partially collapse said second segment without the use of a stator so as to transmit fluids through said conduit by peristaltic movement, said first segment being located such that said first segment is not engaged by said rollers as said rollers are rotated and such that said rollers engage said second segment substantially adjacent to said first segment, and mounting means for mounting said conduit about said rollers and engaging said inlet and outlet ends thereof.

12. A pump conduit for a peristaltic pump including a frame having a plurality of rollers and carrier means for carrying said rollers in spaced apart relation along a predetermined path, drive means for causing movement of said carrier means thereby inducing said rollers to move along said predetermined path, said conduit being flexible and comprising unitarilly formed first and second segments located between an inlet end and an outlet end, said first segment being collapsed and a passageway therethrough being substantially completely occluded in a free condition when pressure within said first segment is equal to pressure acting on the outside of said first segment thereby preventing the transmission of fluids therethrough, said first segment assuming an inflated condition having an unobstructed passageway when pressure within said first segment is greater than the pressure acting on the outside of said first segment thereby permitting the transmission of fluids therethrough, said second segment being biased to exhibit an inflated condition with an open passage therethrough in a free condition when pressure within said second segment is equal to pressure acting on the outside of said first segment thereby permitting the transmission of fluid therethrough.

13. A conduit as set forth in claim 12 wherein said second segment is longer in length than said first segment.

14. A conduit as set forth in claim 12 wherein said first segment exhibits in its free condition a radius of curvature approaching zero at its side edges.

15. A conduit as set forth in claim 12 wherein said first segment is substantially flat in its free condition.

16. A conduit as set forth in claim 12 wherein said second segment including portions generally defining edges, said second segment exhibiting an internal radius of curvature approaching zero at said edges when in its free condition.

17. A conduit as set forth in claim 12 wherein said first segment is located upstream from said second segment.

\* \* \* \* \*